United States Patent [19] [11] 4,323,682
Jan et al. [45] Apr. 6, 1982

[54] QUINOXALINES AND THEIR USE IN PHOTOGRAPHIC PROCESSES

[75] Inventors: Gérald Jan; Remon Hagen; John Lenoir, all of Marly, Switzerland

[73] Assignee: Ciba Geigy AG, Basel, Switzerland

[21] Appl. No.: 88,727

[22] Filed: Oct. 26, 1979

Related U.S. Application Data

[60] Division of Ser. No. 15,384, Feb. 26, 1979, Pat. No. 4,202,698, which is a continuation-in-part of Ser. No. 799,020, May 20, 1977, abandoned.

[30] Foreign Application Priority Data

May 24, 1976 [CH] Switzerland .................. 6521/76

[51] Int. Cl.³ ............................................. C07D 241/42
[52] U.S. Cl. ...................................... 544/353; 544/337
[58] Field of Search ............................. 544/353, 337

[56] References Cited

U.S. PATENT DOCUMENTS

| | | | |
|---|---|---|---|
| 2,221,793 | 11/1940 | Gaspar | 95/6 |
| 3,429,705 | 2/1969 | Piller et al. | 96/53 |
| 3,453,365 | 7/1969 | Lane | 544/353 |
| 3,457,074 | 7/1969 | Wilson | 96/53 |
| 3,656,953 | 4/1972 | Schlunke | 96/53 |
| 3,767,402 | 10/1973 | Schlunke | 96/53 |
| 3,796,576 | 3/1974 | Schlunke | 96/53 |
| 3,963,492 | 6/1976 | Marthaler | 96/53 |
| 4,001,017 | 1/1977 | Baumann et al. | 544/353 |
| 4,014,698 | 3/1977 | Marthaler | 96/53 |

OTHER PUBLICATIONS

Sergeev, Chem. Abs. 88, 152667c (1978).
Jan et al., Chem. Abs. 88, 113314r (1977).

Primary Examiner—Mark L. Berch
Attorney, Agent, or Firm—Sprung, Felfe, Horn, Lynch & Kramer

[57] ABSTRACT

Quinoxalines of the formula

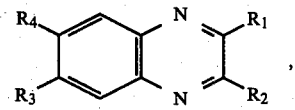

are provided, in which $R_1$ and $R_2$ independently are lower alkyl $R_3$ is lower alkyl, $-CH_2OR_5$, $-CH_2NRR'$, $-CH_2OCOR$, $-CH_2Cl$, $-CH_2Br$, $-CH_2SR$, $-CH_2O(CH_2)_pOR$, $-CH_2PO(OR_5)_2$, $-CH_2PO(OR_6)_2$, $-CH_2SO_3R_6$, $-O(CH_2)_mOR$, $-O(CH_2)_pSO_3R_6$ or $-(OCH_2CH_2)_nOAr$, $R_4$ is hydrogen, lower alkyl or alkoxy when $R_3$ is other than lower alkyl, or $R_4$ is $-OH$, $-NRR'$, $-NHCOR$, $-NHCOAr'$, $-NHSO_2R_5$ or $-NHSO_2Ar'$, R and R' independently are hydrogen or lower alkyl, $R_5$ is lower alkyl, $R_6$ is hydrogen, an alkali metal cation or $-N\oplus(R)_4$, Ar is aryl or sulphonated aryl, Ar' is aryl or substituted aryl, m is 3 or 4, n is 1 to 3 and p is 2 to 4. The quinoxalines are useful as bleach catalysts, especially as dye bleach catalysts, for the photographic silver dye bleach process.

3 Claims, No Drawings

QUINOXALINES AND THEIR USE IN PHOTOGRAPHIC PROCESSES

This is a division, of application Ser. No. 15,384, filed Feb. 26, 1979 which in turn is a continuation-in-part of application Ser. No. 799,020 filed May 20, 1977, now abandoned.

The present invention relates to new quinoxalines of the formula

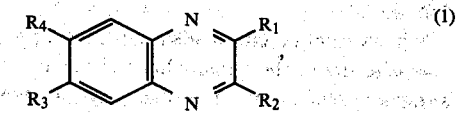

in which $R_1$ and $R_2$ independently are alkyl with 1 to 5 carbon atoms, $R_3$ is alkyl with 1 to 5 carbon atoms, $-CH_2CR_5$, $-CH_2NRR'$, $-CH_2OCOR$, $-CH_2Cl$, $-CH_2Br$, $-CH_2SR$, $-CH_2O(CH_2)_pOR$, $-CH_2PO(OR_5)_2$, $-CH_2PO(OR_6)_2$, $-CH_2SO_3R_6$, $-O(CH_2)_mOR$, $-O(CH_2)_pSO_3R_6$ or $-(OCH_2CH_2)_nOAr$, $r_4$ is hydrogen or alkyl with 1 to 5 carbon atoms or alkoxy of 1 to 4 carbon atoms, when $R_3$ is other than an alkyl radical with 1 to 5 carbon atom, or $R_4$ is $-OH$, $-NRR'$, $-NHCOR$, $-NHCOR$, $-NHCOAr'$, $-NHSO_2R_5$ or $-NHSO_2Ar'$, R and R' independently are hydrogen or alkyl with 1 to 4 carbon atoms, $R_5$ is alkyl with 1 to 4 carbon atoms, $R_6$ is hydrogen, an alkali metal cation or $-N^\oplus(R)_4$, Ar is aryl or sulphonated aryl, Ar' is aryl or substituted aryl, m is 3 or 4, n is 1 to 3 and p is 2 to 4.

The radicals $R_1$ and $R_2$ independently are alkyl with 1 to 5 carbon atoms, such as, for example, methyl, ethyl, n- and iso-propyl, n- and iso-butyl, tert.-butyl or amyl, ethyl and especially methyl being preferred.

If the radical $R_3$ is alkyl with 1 to 5 carbon atoms, these substituents can be the same as those indicated for $R_1$ and $R_2$.

If $R_3$ represents a radical which contains R or R' as further substituents, these substituents as a rule denote hydrogen or straight-chain or branched alkyl with 1 to 4 carbon atoms, so that $R_3$ can be, for example, $-CH_2NH_2$, $-CH_2N(CH_3)_2$, $-CH_2NHC_4H_9$, $-CH_2OCOH$, $-CH_2OCOCH_3$, $-CH_2OCOC_2H_5$, $-CH_2OCOC_4H_9$, $-CH_2SH$, $-CH_2SCH_3$, $-CH_2SC_2H_5$, $-CH_2SC_3H_7$, $-CH_2SC_4H_9$, $-CH_2OCH_2CH_2OH$, $-CH_2OCH_2CH_2OC_2H_5$, $-CH_2OCH_2CH_2OC_3H_7$, $-CH_2OCH_2CH_2OC_4H_9$, $-CH_2O(CH_2)_3OH$, $-CH_2O(CH_2)_3OCH_3$, $-CH_2O(CH_2)_4OCH_3$, $-CH_2O(CH_2)_3OC_2H_5$, or $-CH_2O(CH_2)_3OC_4H_9$. The substituent $R_5$ can be straight-chain or branched alkyl with 1 to 4 carbon atoms, so that further possible radicals $R_1$ are, for example, $-CH_2OCH_3$, $-CH_2OC_2H_5$, $-CH_2OC_3H_7$ (n- and iso-), $-CH_2OC_4H_9$ (n-, iso- or tertiary), $-CH_2PO(OCH_3)_2$, $-CH_2PO(OC_2H_5)_2$, $-CH_2PO(OC_3H_7)$ or $-CH_2PO(OC_4H_9)$. As well as hydrogen, the substituent $R_6$ can be an alkali metal cation, for example a lithium, sodium or potassium cation, as well as an ammonium radical, such as, for example, $-N^\oplus H_4$ or $-N^\oplus(CH_3)_4$.

Those radicals $R_3$ in which R and R' are hydrogen or methyl, $R_5$ is methyl and $R_6$ is hydrogen, a sodium or potassium cation or $-N^\oplus H_4$ are preferred.

Further radicals $R_3$ can be $-O(CH_2)_3OH$, $-O(CH_2)_4OH$, $-O(CH_2)_3OCH_3$, $-O(CH_2)_3OC_2H_5$, $-O(CH_2)_3OC_3H_7$, $-O(CH_2)_3OC_4H_9$, and also $-(OCH_2CH_2)_{1-3}OC_6H_5$, $-(OCH_2CH_2)_{1-3}OC_6H_5SO_3H$ and $-CH_2Cl$ and $-CH_2Br$.

The radical $R_4$ is hydrogen or alkyl with 1 to 5 carbon atoms only when the radical $R_3$ is not an alkyl radical with 1 to 5 carbon atoms. If $R_4$ is alkyl, possible radicals are straight-chain and branched radicals, such as, for example, methyl, ethyl, propyl, isopropyl, butyl, isobutyl, amyl or isoamyl. Further radicals $R_4$ can be, for example, $-OH$, $-OCH_3$, $-OC_2H_5$ or $-OC_3H_7$, $-OC_4H_9$; $-NH_2$, $-NHCH_3$, $-NHC_2H_5$, $-NHC_3H_7$, $-NHC_4H_9$ or $-N(CH_3)_2$; $-NHCOH$, $-NHCOCH_3$, $-NHCOC_2H_5$, $-NHCOC_3H_7$ or $-NHCOC_4H_9$; $-NHSO_2CH_3$, $-NHCOAr'$ or $-NHSO_2Ar'$, wherein Ar' is an aryl radical, especially a phenyl or naphthalene radical, or a substituted aryl radical, possible substituents being halogen, such as, in particular, fluorine, chlorine and bromine, lower alkyl and alkoxy, such as, for example, methyl and ethyl or methoxy and ethoxy, and also carboxyl ($-COOH$) or sulphonic acid ($-SO_3H$), it being possible for these also to be in the form of a salt, and carboxylic acid ester and sulphonic acid ester and nitro.

Those quinoxalines of the formula (1) in which $R_1$ and $R_2$ independently are methyl or ethyl, $R_3$ has the indicated meaning and $R_4$ is hydrogen or alkyl with 1 to 5 carbon atoms when $R_3$ is other than alkyl with 1 to 5 carbon atoms, or is $-OH$, $-NRR'$, $-NHCOR$ or $-NHSO_2R_5$, in which R and R' indpendently are hydrogen or alkyl with 1 to 4 carbon atoms are preferred.

The quinoxalines of the formula

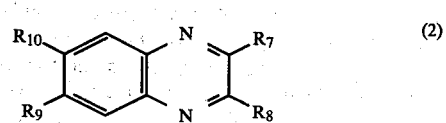

in which $R_7$ and $R_8$ independently are methyl or ethyl, $R_9$ is alkyl with 1 to 5 carbon atoms and $R_{10}$ is $-OH$, $-NRR'$, $-NHCOR$ or $-NHSO_2R_5$ and R and R' independently are hydrogen or alkyl with 1 to 4 carbon atoms and $R_5$ has the indicated meaning are of particular interest.

Particularly suitable quinoxalines also correspond to the formulae

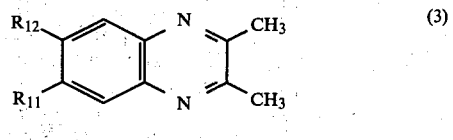

and

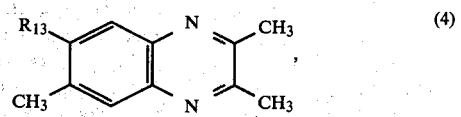

in which $R_{11}$ is methyl or ethyl, $R_{12}$ is $-OH$, $-NR''R'''$, $-NHCOCH_3$ or $-NHSO_2CH_3$, $R_{13}$ is $-OH$, $NH_2$ or $-NHCOCH_3$ and R'' and R''' independently are hydrogen or methyl.

Furthermore, quinoxalines which correspond to the formula

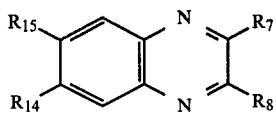
(5)

in which $R_7$ and $R_8$ have the indicated meanings, $R_{14}$ is —CH$_2$OR$_5$, —CH$_2$NRR', CH$_2$OCOR, —CH$_2$Cl, —CH$_2$Br, —CH$_2$SR, —CH$_2$O(CH$_2$)$_p$OR, —CH$_2$PO(OR$_5$)$_2$, —CH$_2$PO(OR$_6$)$_2$, —CH$_2$SO$_3$R$_6$, —O(CH$_2$)$_m$OR, —O(CH$_2$)$_p$SO$_3$R$_6$ or —(OCH$_2$CH$_2$)$_n$OAr, $R_{15}$ is hydrogen or alkyl with 1 to 5 carbon atoms, —OH or —OCH$_3$, R and R' independently are hydrogen or alkyl with 1 to 4 carbon atoms, R$_5$ is alkyl with 1 to 4 carbon atoms, R$_6$ is hydrogen, an alkali metal cation or —N$^\oplus$(R)$_4$, Ar is aryl or sulphonated aryl, m is 3 or 4, n is 1 to 3 and p is 2 to 4, are also particularly valuable.

Particularly preferred quinoxalines of the formula (5) are, now, those compounds which correspond to the formulae

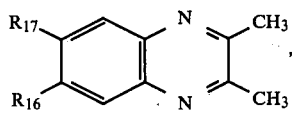
(6)

in which $R_{16}$ is —CH$_2$Cl, —CH$_2$Br, —CH$_2$OCH$_3$, —CH$_2$OCOH, —CH$_2$OCOCH$_3$, —CH$_2$NR''R''', —CH$_2$SO$_3$R$_6$, —CH$_2$O(CH$_2$)$_p$OH, —CH$_2$O(CH$_2$)$_p$OCH$_3$, —O(CH$_2$)$_p$SO$_3$R$_6$ or —(OCH$_2$CH$_2$)$_n$OAr, $R_{17}$ is hydrogen, hydroxyl, methyl, ethyl or methoxy, R$_6$ is hydrogen, an alkali metal cation or —N$^\oplus$(R)$_4$ and R is hydrogen or alkyl with 1 to 4 carbon atoms, R'' and R''' independently are hydrogen or methyl, Ar is aryl or sulphonated aryl, n is 1 to 3 and p is 2 to 4, and

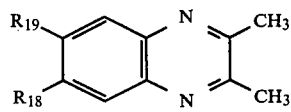
(7)

in which $R_{18}$ is —CH$_2$Br, —CH$_2$OCH$_3$, —CH$_2$OCOH, —CH$_2$OCOCH$_3$, —CH$_2$NH$_2$, —CH$_2$SO$_3$R$_6$, —O(CH$_2$)$_p$SO$_3$R$_6$, —(OCH$_2$CH$_2$)$_n$OC$_6$H$_5$ or —(OCH$_2$CH$_2$)$_n$OC$_6$H$_4$SO$_3$R$_6$, $R_{16}$ is hydrogen, methyl, hydroxyl or methoxy, R$_6$ is hydrogen, an alkali metal cation or —N$^\oplus$(R)$_4$, R is hydrogen or alkyl with 1 to 4 carbon atoms, n is 1 to 3 and p is 2 to 4.

The quinoxalines of the formula (1) are appropriately manufactured in a manner which is in itself known (in this context compare J. C. E. Simpson, Condensed Pyridazine and Pyrazine Rings, in A. Weissberger, The Chemistry of Heterocyclic Compounds, J. Wiley & Sons, New York 1953, 203 et seq.; A. R. Katritzky, Advances in Heterocyclic Chemistry Volume 2, in G. W. H. Cheeseman, Recent Advances in Quinoxaline Chemistry, Academic Press, New York and London 1963, 203 et seq. and Y. T. Pratt, The Quinoxalines, in R. C. Elderfield, Heterocyclic Compounds Volume 6, J. Wiley & Sons, New York 1957, 455 et seq.) by a condensation reaction of an aromatic 1,2-diamine with a 1,2-dicarbonyl compound. In place of the diamine, it is also possible to use the corresponding, considerably more stable o-nitroaniline or the corresponding o-dinitro compound or the corresponding o-arylazoaniline, which can be reduced to the desired diamine and then reacted, without intermediate isolation, to give the quinoxaline. Correspondingly substituted benzfuroxanes and their reduction products (benzfurazanes) can also be reduced via intermediate stages to 1,2-diamines (F. B. Mallory & S. P. Varimbi, J. Org. Chemistry 28, 1,656 et seq. (1963)) and the diamines thus accessible subjected to a condensation reaction to give quinoxalines. In place of the 1,2-dicarbonyl compound, α-oximinoketones can also be reacted with 1,2-diamines to give quinoxalines (in this context compare J. C. E. Simpson, loc. cit.).

The present invention also relates to a process for the manufacture of the quinoxalines of the formula (1). The process is characterised in that aromatic diamines of the formula

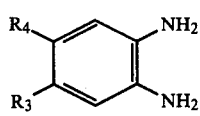
(8)

in which $R_3$ and $R_4$ have the indicated meanings, are subjected to a condensation reaction with 1,2-dicarbonyl compounds of the formula

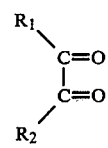
(9)

or α-oximinoketones of the formula

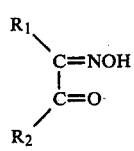
(10)

in which $R_1$ and $R_2$ have the indicated meanings.

The condensation reaction is generally carried out in a solvent, for example, glacial acetic acid, 2-methoxyethanol, ethyl acetate, methanol or water, at temperatures of 5° to 100° C.

With this process the new compounds as a rule precipitate out when the reaction mixture is cooled after the end of the reaction; otherwise they are obtained in good yield by distilling off the solvent and filtering off as well as optionally recrystallising or purifying by chromatography.

The manufacture of the quinoxalines of the formulae (2) and (5) is carried out as indicated by subjecting an aromatic diamine of the formulae

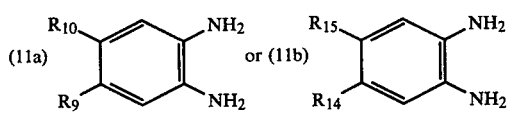

to a condensation reaction with a 1,2-dicarbonyl compound of the formula

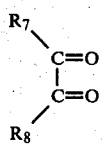 (12)

or with an α-oximinoketone of the formula

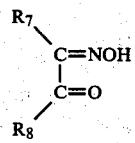 (13)

The radicals $R_7$, $R_8$, $R_9$, $R_{10}$, $R_{14}$ and $R_{15}$ have the indicated meanings.

For the manufacture of the quinoxalines of the formulae (3) and (4), corresponding diamines of the formula

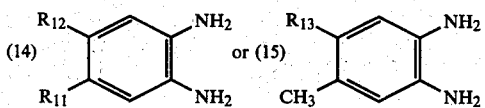

are reacted with diacetyl of the formula

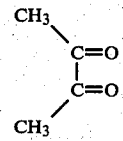 (16)

or α-oximinobutan-2-one

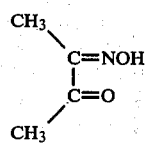 (17)

The radicals $R_{11}$ and $R_{12}$ have the indicated meanings. Quinoxalines of the formulae (6) and (7) are manufactured analogously.

It has proved advantageous to manufacture quinoxalines of the formula (1) in which the radical $R_3$ is substituted in the α-position from the corresponding 6-methylquinoxalines by bromination or chlorination of the 6-methyl group and by subsequent replacement of the halogen atoms, using suitable Lewis bases.

Examples of Lewis bases which can be used are: primary and secondary amines, mercaptides, potassium phthalimide, guanidine, thiourea derivatives, alcoholates, phosphites, sulphites, hydroxy compounds (hydroxides) and anions of carboxylic acids or sulphinic acids.

The alkoxy- and sulphoalkoxy-quinoxalines can appropriately be manufactured from the corresponding hydroxy compounds, for example 6-hydroxy-2,3-dimethylquinoxaline. These compounds can then be reacted in the customary manner in a suitable solvent (for example water, dimethylformamide or alcohols), in the presence of a base (for example potassium hydroxide or sodium hydroxide), with an alkylating agent (for example dimethyl sulphate or propanesultone).

6-(4'-Sulphophenoxyalkoxy)-quinoxalines can preferably be obtained by sulphonation of the corresponding phenoxyalkoxyquinoxalines.

The quinoxalines which are substituted in the 7-position by carboxamide radicals or sulphonamide radicals can as a rule be obtained by acylation of the corresponding aminoquinoxalines with carboxylic acid and anhydrides or carboxylic acid halides or sulphonic acid halides, especially the chlorides.

The quinoxalines can as a rule be obtained in better yield and higher purity if the condensation reaction is carried out in a nitrogen atmosphere.

Examples of starting materials which can be used for one of the said syntheses are the compounds named below:

1,2-Dicarbonyl compound, α-oximinoketones

Diacetyl, 3-oximinobutan-2-one, hexane-3,4-dione, 4-oximino-3-hexanone and 2,3-pentanedione.

LEWIS BASES

Sodium methylate, sodium ethylate, potassium methylate, potassium ethylate, potassium propylate, potassium isopropylate, potassium butylate, potassium isobutylate, potassium tertiary butylate, sodium mercaptide, potassium mercaptide, sodium methylmercaptide, potassium methylmercaptide, sodium ethylmercaptide, potassium ethylmercaptide, thiourea, sodium acetate, potassium xanthate, potassium acetate, sodium propionate, potassium propionate, sodium 3-methoxypropylate, potassium 3-methoxypropylate, sodium 4-methoxybutylate, potassium 4-methoxybutylate, sodium butyrate, potassium butyrate, sodium methoxyethylate, potassium 2-methoxyethylate, sodium 2-ethoxyethylate, potassium 2-ethoxyethylate, sodium monotetramethyleneglycolate, potassium monotetramethyleneglycolate, sodium monotrimethyleneglycolate, potassium monotrimethyleneglycolate, sodium monoglycolate, potassium monoglycolate, ammonia, potassium phthalimide, guanidine, dimethylamine, diethylamine, dipropylamine, methylamine, ethylamine, propylamine, sodium sulphite, potassium sulphite, water, sodium hydroxide, potassium hydroxide, trimethyl phosphite, triethyl phosphite, tributyl phosphite and tripropyl phosphite.

O-NITROANILINES AND O-DINITROBENZENES, 1,2-DIAMINES AND O-ARYLAZOANILINES 1,2-Dinitro-4-(3-sulpho-1-propoxy)-benzene, 1,2-diamino-4-(3-sulpho-1-propoxy)-benzene, 1-amino-2-nitro-4-(3-sulpho-1-propoxy)-benzene, 2-amino-1-nitro-4-(3-sulpho-1-propoxy)-benzene, 1,2-dinitro-4-(2-sulpho-ethoxy)-benzene, 1,2-diamino-4-(2-sulphoethoxy)-benzene, 1-amino-2-nitro-4-(2-sulpho-ethoxy)-benzene, 2-amino-1-nitro-4-(2-sulphoethoxy)-benzene, 1,2-dinitro-4-(4-sulpho-1-butoxy)-benzene, 1,2-diamino-4-(4-sulpho-1-butoxy)-benzene, 1-amino-2-nitro-4-(4-sulpho-1-butoxy)-benzene, 2-amino-1-nitro-4-(4-sulpho-1-butoxy)-benzene, 1-methoxy-4,5-dinitro-2-(2-sulphoethoxy)-benzene, 1-methoxy-4,5-dinitro-2-(3-sulpho-1-propoxy)-benzene, 1-methoxy-4,5-dinitro-2-(4-sulpho-1-butoxy)-benzene, 4,5-diamino-1-methoxy-2-(2-sulphoethoxy)-benzene, 4,5-diamino-1-methoxy-2-(3-sulpho-1-propoxy)-benzene, 4,5-diamino-1-methoxy-2-(4-sulpho-1-butoxy)-benzene, (4)(5)-amino-1-methoxy-(5)(4)-nitro-2-(2-sulphoethoxy)-benzene, (4)(5)-amino-1-methoxy-(5)(4)-nitro-2-(3-sulpho-1-propoxy)-benzene, (4)(5)-amino-1-methoxy-(5)(4)-nitro-2-(4-sulpho-1-butoxy)-benzene, 1-amino-4-hydroxymethyl-2-nitrobenzene, 1-hydroxymethyl-3,6-dinitrobenzene, 1,2-diamino-4-hydroxymethyl-benzene, 1-methoxymethyl-3,4-dinitro-benzene, 1,2-diamino-4-methoxymethyl-benzene, 1-amino-4-methoxymethyl-2-nitro-benzene, 2,4,5-triamino-toluene, 2,4-diamino-5-nitro-toluene, 2-amino-4,5-dinitro-toluene, 2-methylsulphonamido-4,5-dinitrotoluene, 2-acetamido-4,5-dinitro-toluene, 2,4-diamino-5-phenylazo-toluene, 2,4-diamino-5-(4-sulphophenylazo)-toluene, 2,4-diamino-5-(4-chlorophenylazo)-toluene, 2,4-diamino-5-(4-methylphenylazo)-toluene, 2-hydroxy-4,5-dinitro-toluene, 4,5-diamino-2-hydroxy-toluene, 4-amino-2-hydroxy-5-phenylazo-toluene, 4-amino-2-hydroxy-5-(4-sulphophenylazo)-toluene, 4-amino-2-hydroxy-5-(4-chlorophenylazo)-toluene, 4-amino-2-hydroxy-5-(4-methylphenylazo)-toluene, 2-methoxy-4,5-dinitro-toluene, 4,5-diamino-2-methoxy-toluene, 4,5-dinitro-2-(2-sulphoethoxy)-toluene, 4,5-diamino-2-(2-sulphoethoxy)-toluene, 4,5-dinitro-2-(3-sulpho-1-propoxy)-toluene, 4,5-diamino-2-(3-sulpho-1-propoxy)-toluene, 4,5-dinitro-2-(4-sulpho-1-butoxy)-toluene, 4,5-diamino-2-(4-sulpho-1-butoxy)-toluene, 2-nitro-4-(2-phenoxyethoxy)-aniline, 3,4-dinitro-1-(2-phenoxyethoxy)-benzene and 2-nitro-4-[2-(4-sulphophenoxy)ethoxy]-benzene.

Quinoxalines (for halogenation of the side chains)

2,3,6-Trimethyl-quinoxaline and 2,3,6,7-tetramethyl-quinoxaline.

Amino- and hydroxy-quinoxalines (for example for alkylation and acylation)

6-Hydroxy-2,3-dimethyl-quinoxaline, 6-hydroxy-2,3,7-trimethyl-quinoxaline, 6-amino-2,3,7-trimethyl-quinoxaline and 6-hydroxy-7-methoxy-2,3-dimethyl-quinoxaline.

Alkylating agents, acylating agents and sulphonic acid chlorides

The sodium salt of 2-bromo-ethanesulphonic acid, the sodium salt of 2-chloro-ethanesulphonic acid, propanesultone, butanesultone, methyl iodide, ethyl iodide, ethyl bromide, acetic anhydride, acetyl chloride, methanesulphonyl chloride, benzenesulphonyl chloride and p-toluenesulphonyl chloride.

Quinoxalines (for example for sulphonation)

2,3-Dimethyl-6-(2-phenoxy-ethoxy)-quinoxaline.

The quinoxalines of the formula (1) can be used in a processing bath, preferably an acid bleach bath, as bleach catalysts for the silver dye bleach process and especially in an acid dye bleach bath as dye bleach catalysts.

They are particularly readily soluble in acid baths and have an excellent action as dye bleach catalysts.

6-(Hydroxymethyl)-2,3-dimethylquinoxaline (C.A. 51, 433a) and 6-(2-hydroxyethoxy)-2,3-dimethylquinoxaline (C.A. 48, 884d) are dye bleach catalysts which also have a good action.

They can be used either on their own or in the presence of other customary dye bleach catalysts. It is also possible for different quinoxalines of the formula (1) to be used at the same time in the dye bleach bath. Finally, it is also possible to employ the quinoxalines of the formula (1) together with other measures which promote dye bleaching, such as, for example, by adding organic solvents or bleaching accelerators.

The quinoxalines of the formula (1) are, furthermore, also suitable for processes for the production of coloured photographic images by the silver dye bleach process as well as also for processes for rapid processing of silver dye bleach materials. In these processes, for example, the dye bleach bath, the silver bleach bath and, optionally, also the fixing bath are combined.

As a rule, these combined baths then contain bleaching accelerators, such as, for example, phosphines, oxidising agents and antioxidants (compare DT-OS No. 2,448,433) in addition to the said quinoxalines.

The present invention thus also relates to a process for the production of coloured photographic images by the silver dye bleach process on materials which contain, on a substrate, at least one silver halide emulsion layer with a dyestuff which can be bleached imagewise, by exposure and subsequent processing by developing the silver image, dye bleaching, silver bleaching, silver fixing and washing, wherein the dye bleaching and/or silver bleaching is carried out in the presence of at least one quinoxaline of the formula (1) as the bleach catalyst, as well as also to a process for the rapid processing of silver dye bleach materials which comprises the following process steps (1) silver developing, (2) dye bleaching and silver bleaching, (3) silver fixing and (4) washing.

The latter process is characterised in that, using treatment baths corresponding to the treatment stages (1) to (4), and using them in the sequence (1) to (4), a bleach bath which contains (a) a strong acid, (b) a water-soluble iodide, (c) a water-soluble oxidising agent, (d) an antioxidant and (e) as the dye bleach catalyst, a quinoxaline of the formula (1), preferably in an amount of 0.5 to 5 g per liter, and (f) optionally a bleach accelerator is used for the combined dye bleaching and silver bleaching (2) and that the entire processing, from entry into the first bath (1) to leaving the final bath, is carried out at temperatures of 20° to 90° C.

Moreover, the processing can also be so carried out that the entire processing, from entry into the first bath (1) to leaving the final bath, takes at most 10 minutes and the dwell time in the individual baths is at most 2 minutes.

The invention also relates to photographic processing baths, especially dye bleach baths or combined dye bleach and silver bleach baths, for the silver dye bleach process which contain, as the bleach catalyst, at least one quinoxaline of the formula (1). In general, the aqueous dye bleach formulations required for the processing are allowed to act on the material in the form of dilute aqueous solutions which contain components (a) to (e) and optionally (f).

However, other methods, for example use in paste form, are also conceivable. The temperature of the baths during processing, and especially also the temperature of the bleach bath, can in general be between 20° and 60° C. and, of course, the requisite processing time is shorter at a higher temperature than at a lower temperature.

The aqueous bleaching formulation according to the present invention can also be prepared in the form of a liquid concentrate, especially an aqueous concentrate, and, because of its good stability, can be stored for a prolonged period. It is advantageous to use, for example, two liquid concentrates, of which one contains the strong acid (a) and the oxidising agent (c) and the other contains the remaining components (b), (d), (e) and optionally (f), it being possible to add an additional solvent, such as ethyl alcohol or propyl alcohol, ethylene glycol methyl ether or ethylene glycol ethyl ether, to the latter concentrate in order to improve the solubility, especially of component (e).

These concentrates can optionally be diluted by dilution with water or with a mixture of water and an organic solvent.

For silver developing in process step (1) it is possible to use baths of customary composition, for example those which contain hydroquinone and, if desired, additionally 1-phenyl-3-pyrazolidinone, as the developer substance.

The bleach bath (2) preferably contains sulphuric acid or sulphamic acid as the strong acid. The pH value of the bleach bath (2) is, in particular, not greater than 2 and preferably not greater than 1. The water-soluble iodides are as a rule alkali metal iodides, especially sodium iodide and potassium iodide. The amount of iodide is about 2 to 50 g/l of bleach bath.

Water-soluble, aromatic nitro and dinitro compounds are appropriately used as the oxidising agent. The use of such oxidising agents with a view to thus influencing the colour balance and the contrast in the images produced by the dye bleach process has already been described in German Pat. No. 735,672, in British Pat. Nos. 539,190 and 539,509 and in Japanese Pat. No. 22,673/69.

Particularly advantageous oxidising agents are the compounds of the formula

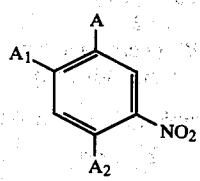

(18)

in which A is $-CO_2M$ or $-SO_3M$, $A_1$ is hydrogen, hydroxyl, amino($NH_2$), methyl or methoxy, $A_2$ is hydrogen, methyl, methoxy or trifluoromethyl and M is hydrogen, an alkali metal cation or $N^{\oplus}(R)_4$, in which R has the indicated meaning.

Examples of oxidising agents which can be used are the following aromatic nitro compounds: 3-nitrobenzenesulphonic acid, 3-nitrobenzoic acid, 2-amino-5-nitrobenzoic acid, 2-amino-5-nitrobenzenesulphonic acid, 2-amino-4-methyl-5-nitrobenzenesulphonic acid, 2-amino-4-methoxy-5-nitrobenzenesulphonic acid, 4-nitrophenol-2-sulphonic acid, 2-hydroxy-5-nitrobenzoic acid, 5-methyl-4-nitrophenol-2-sulphonic acid, 4-nitrotoluene-2-sulphonic acid, 4-nitroanisole-2-sulphonic acid, 2,4-dimethyl-5-nitrobenzenesulphonic acid, 5-methyl-4-nitro-anisole-2-sulphonic acid and 2-nitrotoluene-4-sulphonic acid; the following products can also be used: 2-amino-4-trifluoromethyl-5-nitrobenzenesulphonic acid, 2-amino-3-methyl-5-nitrobenzenesulphonic acid, 2-amino-3-methoxy-5-nitrobenzenesulphonic acid, 2-amino-5-methoxy-3-nitrobenzenesulphonic acid, 3-amino-4-methyl-5-nitrobenzenesulphonic acid, 2,4-diamino-5-nitrobenzenesulphonic acid, 2-amino-4-nitrobenzenesulphonic acid, 2-amino-5-methoxy-4-nitrobenzenesulphonic acid, 3-amino-4-methoxy-6-nitrobenzenesulphonic acid, 2-amino-5-methyl-3-nitrobenzenesulphonic acid, 3-nitro-aniline, 2-methyl-4-nitroaniline, 3-amino-7-nitronaphthalene-1,5-disulphonic acid, 2-amino-4-nitrophenol-6-sulphonic acid, 2-nitrophenol-4-sulphonic acid, 2-nitroanisole-4-sulphonic acid, 4-chloro-3-nitrobenzenesulphonic acid, 2-chloro-5-nitrobenzenesulphonic acid, 2,4-dinitrobenzenesulphonic acid, 2,6-dinitrotoluene-4-sulphonic acid, 2,4-dimethyl-3-nitrobenzenesulphonic acid, 2,4,6-trimethyl-3-nitrobenzenesulphonic acid, 2-amino-4-chloro-5-nitrobenzenesulphonic acid, 2-amino-3-chloro-5-nitrobenzenesulphonic acid, 2-nitrobenzoic acid, 3-nitrophthalic acid, 4-nitrophthalic acid, 3-[3'-nitrophenoxy]-propanesulphonic acid and (2'-dimethylamino)-ethyl 4-nitrobenzoate.

The nitrobenzenecarboxylic acids or nitrobenzenesulphonic acids can be used either in the form of free acids or in the form of their metal salts, especially in the form of the alkali metal salts or alkaline earth metal salts, or in the form of ammonium salts.

The amount of oxidising agent in the bleach bath can be in the range from 1 to 30 g/l.

Organic mercapto compounds are advantageously used as antioxidants. It has proved particularly advantageous to use the compounds of the formulae

  (19)

  (20)

in which q denotes an integer with a value of 2 to 12, B denotes a sulphonic acid group or carboxylic acid group and m denotes one of the numbers 3 and 4. Mercapto compounds which can be used as antioxidants are described in DT-OS No. 2,258,076 and in DT-OS No. 2,423,814. Other antioxidants are e.g. thioglycerol or thiomalic acid or reductones such as ascorbic acid (U.S. Pat. No. 36 20 744). The amount of antioxidant is about 0.5 to 10 g/l.

The pH value of the bleach bath (2) should be less than 2 and this can be achieved without difficulty by the presence of sulphuric acid or sulphamic acid, which have already been mentioned. The temperature of the bleach bath, and also of the other treatment baths, is 20° to 90° C. In general it is advantageous to work at temperatures of not more than 60° C. The ratios of the substances (a), (b), (c) and (d) present in the bleach bath can vary within rather wide limits and are appropriately chosen analogously to the ratios for known methods. It is advantageous if the bleach baths contain the indicated, relatively high amount of 0.5 to 5 g of dye bleach catalyst per liter of bath liquid.

The silver fixing bath can be of known and customary composition. The fixer used is, for example, sodium thiosulphate or, advantageously, ammonium thiosulphate, if desired with additives such as sodium bisulphite and/or sodium metabisulphite.

All the baths can contain additives, such as hardeners, wetting agents, optical brighteners and UV-stabilisers.

The process for the rapid processing of silver dye bleach materials can be used, for example, in the production of positive coloured images in automatic copying or recording machines or in the rapid processing of other silver dye bleach materials, such as, for example, for scientific recording and industrial purposes, for example coloured X-ray screen photography.

A transparent, metallic-reflecting material or, preferably, white-opaque material, the carrier of which is not able to absorb any liquid from the baths, can be used as the silver dye bleach material.

The carrier can consist, for example, of optionally pigmented cellulose triacetate or polyester. If it consists of a paper felt this must be lacquer-coated or coated with polyethylene on both sides. The light-sensitive layers are located on at least one side of this carrier, preferably in the known arrangement, that is to say at the bottom a red-sensitised silver halide emulsion layer which contains a cyan azo dyestuff, above this a green-sensitised silver halide emulsion layer which contains a magenta azo dyestuff and on the top a blue-sensitive silver halide emulsion layer which contains a yellow azo dyestuff. The material can also contain sublayers, intermediate layers, filter layers and protective layers, but the total thickness of the layers as a rule should not exceed 20μ.

MANUFACTURING INSTRUCTIONS

General Instruction A

Quinoxalines manufactured from an aromatic 1,2-diamine, a o-nitroaniline compound or a o-dinitrobenzene derivative and a 1,2-dicarbonyl compound A substituted o-dinitrobenzene derivative or the corresponding o-nitroaniline compound is dissolved, or merely suspended, in a suitable solvent such as, for example, ethyl acetate, methanol, ethanol, glacial acetic acid, dimethylformamide, 2-methoxyethanol, 2-ethoxyethanol or water, 1 to 10 percent by weight of a hydrogenation catalyst, such as, for example, a 10% strength palladium-on-charcoal catalyst, are added and the hydrogenation is carried out under normal pressure, with initial warming if necessary. After the reaction has ended, the catalyst is filtered off under nitrogen and at least the equimolar amount of the corresponding diketone is added, under nitrogen, to the filtrate, which is cooled to 0° C. to 10° C. if necessary; in most cases a deepening of the colour takes place when this addition is made. The mixture is then stirred, with warming if necessary, until the reaction has ended and the desired substance is isolated. The product can be purified by recrystallisation from a suitable solvent, distillation or, if necessary, by chromatography or sublimation.

In some cases, sodium hyposulphite in alkaline solution is used as the reducing agent in order to reduce the o-dinitrobenzene derivative or the corresponding o-nitroaniline compound to the 1,2-diaminobenzene derivative.

If the corresponding o-phenylenediamine is easily accessible and in sufficient purity, it is, as described, subjected direct or in the form of its hydrochloride in a suitable solvent, under nitrogen, to a condensation reaction with the diketone. When the hydrochloride is used, it is advisable, in order to neutralise the hydrochloric acid liberated, to add a corresponding amount of sodium acetate or potassium acetate. The compound which are obtained in this way are listed in Table I.

PREPARATION EXAMPLE A-1: (Compound No. 101)

The ammonium salt of 2,3-dimethyl-6-(3-sulpho-1-propoxy)-7-methoxyquinoxaline

Preparation of 1-methoxy-4,5-dinitro-2-(3-sulpho-1-propoxy)-benzene:

Guaiacol is alkylated in dimethylformamide, in the presence of the stoichiometric amount of 30% strength aqueous sodium hyroxide solution, with propanesultone (yield: 87%). The o-(3-sulpho-1-propoxy)-anisole (sodium salt) is converted, in quantitative yield, into the barium salt using a barium chloride solution.

The free acid is liberated by adding the equimolar amount of sulphuric acid, the barium sulphate is then filtered off and the water is removed. The residue is dissolved in an acetic acid/acetic anhydride mixture and nitrated with an excess of 96% strength nitric acid at 100° C. The reaction mixture is discharged into cold water. The pH value of the solution thus obtained is adjusted to 5 with 30% strength aqueous sodium hydroxide solution and an excess of barium chloride is added to the mixture. The barium salt of 1-methoxy-4,5-dinitro-2-(3-sulpho-1-propoxy)-benzene precipitates out. The product is filtered off, washed with acetone and dried in vacuo at 60° C. Yield: 84% of theory.

Analysis: calculated: Ba 17.0 S 7.94 found: Ba 15.8 S 7.50

The free acid is liberated using the equimolar amount of sulphuric acid, the barium sulphate thus formed is filtered off and the water is evaporated. The residue is dissolved in methanol; an excess of an aqueous 28% strength ammonia solution is then added dropwise. The ammonium salt separates out as a yellow precipitate. The precipitate is filtered off, washed with methanol and isopropanol and dried in vacuo at 60° C. The product is obtained in a yield of 71% of theory. Melting point: 243° to 245° C.; the NMR and infrared spectra correspond to the indicated structure.

The compound obtained in this way is reduced as described in instruction A and the reaction product is reacted with diacetyl. The compound of the formula (101) is obtained in 60% yield.

Melting point: 223° to 227° C.

The IR and NMR spectra and also the elementary analysis correspond to the indicated structure.

Preparation example A-2: (Compound No. 102)

1-Amino-2-nitro-4-(2-phenoxy-ethoxy)-benzene

This compound is prepared in a manner which is in itself known (see J. Scarborough, J. Chem. Soc. 1929, 2366 "Preparation of 3-nitro-4-amino-diphenyl ether").

1-Chloro-4-nitrobenzene is reacted in dimethylsulphoxide, in the presence of a base, with ethylene glycol monophenyl ether: 1-nitro-4-(2-phenoxy-ethoxy)-benzene is obtained in 87% yield.

(Melting point: 86° to 87° C.).

1-Nitro-4-(2-phenoxy-ethoxy)-benzene is reduced and the resulting amine is heated in acetic anhydride and glacial acetic acid and nitrated with 70% strength nitric acid. 1-Acetamido-2-nitro-4-(2-phenoxy-ethoxy)-benzene is obtained in 90% yield (melting point: 104° to 106° C.). The amide is hydrolysed with potassium hydroxide in ethanol and the desired nitroamine is obtained in 98% yield (melting point 121° to 123° C.).

The nitroamine thus obtained is reduced and the reaction product is reacted with diacetyl. (Compare Instruction A). The compound of the formula (102) is obtained in 90% yield.

Melting point: 114° to 115° C.

The IR and NMR spectra as well as the elementary analysis correspond to the indicated structure.

General Instruction B

Quinoxaline prepared from an o-arylazoanilien compound

A correspondingly substituted aniline, usually a substituted m-phenylenediamine or a substituted m-aminophenol, is coupled with a suitable aromatic diazonium salt, such as, for example, 4-diazobenzenesulphonic acid. In general, the azo grouping in the resulting dyestuff is reduced, without isolation of the dyestuff, using sodium hyposulphite in alkaline solution at temperature between 40° and 90° C., to give the amine. The pH value of the reaction mixture is brought to 5 to 6 with hydrochloric acid or acetic acid and the diamine formed is then subjected to a condensation reaction with at least the equimolar amount of a diketone, at temperatures of 25° C. to 70° C.

The desired compound is then isolated. The product can be purified by recrystallisation from a suitale solvent, by distillation or, if necessary, by chromatography or sublimation.

If phenyldiazonium salts, 4-methylbenzenediazonium salts or 4-chlorobenzenediazonium salts used, in place of 4-diazobenzenesulphonic acid, for the coupling reaction, the azo grouping formed can also be hydrogenated catalytically to give the amine. (Compare Instruction A).

Compounds which have been synthesised according to these instructions are listed in Table II.

Preparation Example B-1: (Compound No. 104)

6-Amino-2,3,7-trimethyl-quinoxaline 122 g (1 mol) of 2,4-diaminotoluene are mixed with 700 ml of water, 300 g of ice and 83 ml of concentrated hydrochloric acid. The solution is cooled to 0° C. and 218.5 g (1 mol) of moistened 4-diazobenzenesulphonic acid (titre: 77%) are added in portions, whilst stirring.

A red dyestuff forms spontaneously. The pH value of the mixture is kept at 2 to 3 by adding a 30% strength sodium acetate solution. The red suspension is stirred for two hours at 5° C. 200 ml of 30% strength sodium hydroxide solution are then added; the mixture thus obtained is then introduced into a solution of 500 g of sodium hyposulphite monohydrate, 100 ml of 30% strength sodium hydroxide solution and 1,800 ml of water. The mixture is stirred and heated to 70° C. for 30 minutes. The deep red solution loses its colour and a clear brown-yellow solution is obtained. The solution is cooled to 30° C. and the pH value is adjusted to 5 to 6 by adding 300 ml of glacial acetic acid. 90 g (1.05 mols) of diacetyl are added dropwise and the resulting mixture is stirred for 60 minutes. The desired product separates out as a yellow precipitate and this is filtered off. The crude product is suspended in 1,500 ml of water and the suspension is stirred for 10 minutes and then filtered. The resulting product is dried in vacuo at 60° C.

Yield: 141 g (75% of theory). Melting point: 226° to 228° C.

The IR and NMR spectra and the elementary analysis correspond to the indicated structure.

General Instruction C

Quinoxalines manufactured by nucleophilic substitution of α-halogenomethylquinoxalines using Lewis bases:

A 6-(α-halogenomethyl)-quinoxaline is dissolved, or merely suspended, in a suitable solvent, such as, for example, methanol, ethanol, 2-methoxyethanol, 2-ethoxyethanol, dimethylformamide, dimethylsulphoxide, acetonitrile, water, glycol, toluene, chlorobenzene, sulpholane or formamide. The Lewis base, optionally in a suitable solvent, is added to the solution of the 6-(α-halogenomethyl)-quinoxaline, or a solution or suspension of the 6-(α-halogenomethyl)-quinoxaline is added to the solution of the Lewis base. The mixture thus obtained is, if necessary, heated to the desired temperature and the compound formed is isolated. The product is purified by the customary processes.

The compounds which are manufactured according to this instruction is listed in Table III.

General Instruction D

Alkylation or acylation of hydroxy- or amino-quinoxalines

The alkali metal salt of a 6-hydroxyquinoxaline, or a 6-aminoquinoxaline, is dissolved or suspended in a suitable solvent (for example water, dimethylformamide, methanol, ethanol or methylcellosolve or, respectively, dimethylformamide, dimethoxyethane, acetone, pyridine, toluene or chlorobenzene), the solution or suspension is mixed with the alkylating or acylating reagent and the whole is heated to the desired reaction temperature. The product is isolated and purified if necessary. The compounds obtained according to this instruction are listed in Table IV.

Preparation Example D-1: (Compound No. 112)

The sodium salt of 2,3-dimethyl-6-(3-sulpho-1-propoxy)-quinoxaline 8.7 g (50 mmols) of 6-hydroxy-2,3-dimethylquinoxaline are dissolved in 50 ml of dimethylformamide and 6.6 g (50 mmols) of 30% strength sodium hydroxide solution are added. The solution is stirred for 15 minutes and 6.7 g (55 mmols) of propanesultone are then added. The mixture is heated to 65° C. for two hours. It is allowed to cool to room temperature; thereupon the desired product separates as a white precipitate. The mixture is cooled to 0° C. and the precipitate is filtered off and washed with 1,2-dimethoxyethane. The product is dried in vacuo at 60° C. 9.7 g (58% of theory) of a white powder are obtained (the product contains 1 mol of $H_2O$).

The NMR and infrared spectra correspond to the indicated structure.

Further Manufacturing Instructions (E)

Preparation Example E-1: (Compound No. 116)

6-(Bromomethyl)-2,3-dimethoxyquinoxaline is obtained by free radical bromination of 2,3,6-trimethylquinoxaline by means of N-bromosuccinimide. Carbon tetrachloride is used as the solvent and α,α'-azobisisobutyronitrile is used as the catalyst.

Preparation Example E-2: (Compound No. 115)

2,3-Dimethyl-6-[2-(4-sulphophenoxy)-ethoxy]-quinoxaline is obtained from 2,3-dimethyl-6-(2-phenoxy-ethoxy)-quinoxaline (compound 102) by sulphonation using 10% strength oleum.

TABLE I

| No. | Compound | Starting materials | | Reducing agent | Isolation | Yield % | Melting point °C. |
|---|---|---|---|---|---|---|---|
| 101 | CH3O-[structure with N-CH3, N-CH3]-O-(CH2)3-SO3NH4, CH3O | CH3O-[benzene with NO2, NO2]-O(CH2)3-SO3NH4 | (CH3CO)2O | H2/Pd-C/Pt (H2O—CH3OCH2CH2OH) (80:20) | Recrystallisation from ethanol | 60 | 223–227 |
| 102 | C6H5OCH2CH2O-[structure with N-CH3, N-CH3] | C6H5OCH2CH2O-[benzene with NH2, NO2] | (CH3CO)2O | H2/Pd-C CH3COOH | Filtration | 90 | 114–115 |
| 103 | OH, CH3-[structure with N-CH3, N-CH3]-CH3 | CH3-[benzene with NO2, NO2]-OH | (CH3CO)2O | Na2S2O4 H2O/NaOH | Filtration, recrystallisation from propanol | 63 | >275 (decomposition) |

The NMR and infrared spectra of the compounds in this table agree with the indicated structures.

TABLE II

| No. | Compound | Starting materials | Diketone | Isolation/ purification | Yield % | Melting point °C. |
|---|---|---|---|---|---|---|
| 104 | CH3-, H2N- substituted benzodiazine with N=C(CH3)-C(CH3)=N ring | 2-methyl-4-amino-benzenediazonium-4-sulfonate with NH2 | $(CH_3CO)_2$ | Filtration | 75 | 226–228 |
| 105 | HO-, CH3- substituted benzodiazine with N=C(CH3)-C(CH3)=N ring | HO-, CH3- substituted benzenediazonium-4-sulfonate with NH2 | $(CH_3CO)_2$ | Recrystallisation from dimethylformamide | 80 | >275 |

The NMR and infrared spectra of the compounds in this table correspond to the indicated structures.

TABLE III

| No. | Compound | Starting materials | Lewis base solvent | Isolation/ purification | Yield % | Boiling point (b.p.)/ melting point (m.p.) °C. |
|---|---|---|---|---|---|---|
| 106 | CH3COOCH2-substituted benzodiazine (N=C(CH3)-C(CH3)=N) | BrCH2-substituted benzodiazine | $CH_3COOK$ ethanol | Chromatography $SiO_2$/ $CH_3COOC_2H_5$ | 57 | m.p. 64–68 |
| 107 | CH3OCH2-substituted benzodiazine | BrCH2-substituted benzodiazine | $CH_3ONa$ methanol | distillation | 60 | b.p. 100° C./0.2 mm Hg m.p. 58–62 |
| 108 | HOCH2-substituted benzodiazine | BrCH2-substituted benzodiazine | $H_2O/K_2CO_3$ acetonitrile | chromatography $SiO_2$/ $CH_3COOC_2H_5$ | 30 | m.p. 101–104 |

| No. | Compound | Starting materials | Lewis base solvent | Isolation/ purification | Yield % | Melting point °C. |
|---|---|---|---|---|---|---|
| 109 | H2N—CH2-substituted benzodiazine | BrCH2-substituted benzodiazine | (1) Potassium phthalimide/ dimethylformamide/60° C. (2) $N_2H_4$/ ethanol (3) $H^{\oplus}$ | Chromatography $SiO_2$ Ethyl acetate/ methanol | 46 | 93 (hygroscopic) |
| 110 | $H_4NO_3S$—CH2-substituted benzodiazine | BrCH2-substituted benzodiazine | $Na_2SO_3$ water | via the free acid (betain) and neutralisation with ammonia | 49 | 300° (decomposition) |

The NMR and infrared spectra of the compounds in this table agree with the indicated structures. Compound (108) has already been described (J.A. Silk, J. Chem. Soc. 1956, 2,058); however, the preparation from the bromomethyl derivative by means of nucleophilic substitution is simpler than the synthesis route described in the literature.

TABLE IV

| No. | Compound | Starting materials | Alkylating/ acylating agent | Isolation/ purification | Yield % | Melting point °C. |
|---|---|---|---|---|---|---|
| 111 | CH3O-, CH3- substituted benzodiazine with N=C(CH3)-C(CH3)=N | HO-, CH3- substituted benzodiazine | $(CH_3)_2SO_4$ $NaOH/H_2O$ | recrystallisation from ethanol/$H_2O$ | 55 | 143–145 |

TABLE IV-continued

| No. | Compound | Starting materials | Reagent | Isolation purification | Yield % | Melting point °C | |
|---|---|---|---|---|---|---|---|
| 112 | NaO₃S(CH₂)₃O—[quinoxaline with CH₃, CH₃] | HO—[quinoxaline with CH₃, CH₃] | [tetrahydrothiophene SO₂] NaOH/ dimethyl-formamide | filtration | 58 | 200 (decomposition) | crystallises with one mol of H₂O |
| 113 | CH₃CONH—[quinoxaline with CH₃, CH₃, CH₃] | H₂N—[quinoxaline with CH₃, CH₃, CH₃] | acetic anhydride/ toluene | filtration | 71 | 252 | |
| 114 | CH₃SO₂NH—[quinoxaline with CH₃, CH₃, CH₃] | H₂N—[quinoxaline with CH₃, CH₃, CH₃] | CH₃SO₂Cl/ pyridine | via the sodium salt | 47 | 218–219 | |
| 115 | [structure with O(CH₂)₂O, SO₃NH₄, quinoxaline CH₃, CH₃] | [phenoxy(CH₂)₂O quinoxaline CH₃, CH₃] | Oleum 10% | Extraction of the ammonium salt with methanol | 92 | 226–240 (decomposition) | |
| 116 | BrCH₂—[quinoxaline with CH₃, CH₃] | CH₃—[quinoxaline with CH₃, CH₃] | N-bromo-succinimide/CCl₄/ azobis-isobutyronitrile | Evaporation of the solvent and suspension in n-hexane | 55 (yield of crude product 95) | 105–107 | the crude product contains 5% of a different isomer |

The NMR and infrared spectra of the compounds in this table agree with the indicated structures.

APPLICATION EXAMPLES

EXAMPLE 1

The effectiveness of the new quinoxalines as silver dye bleach catalysts is examined with the aid of single layer coatings of the following composition:

8.2 g of gelatine/m²
Molar ratio of silver to dyestuff: 44:1
Maximum transmission density of the dyestuff about 1.4.

The silver halide emulsion used is a bromide/iodide emulsion which contains 2.6 mol% of iodine and has not been spectrally sensitised. One of the following dyestuffs is used: Yellow:

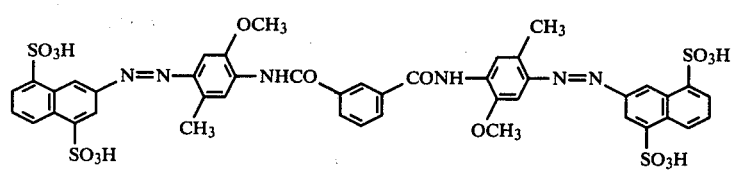
(117)

Magenta:
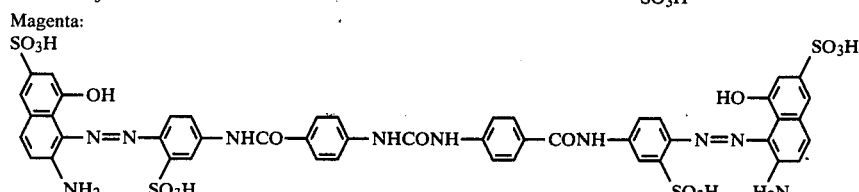
(118)

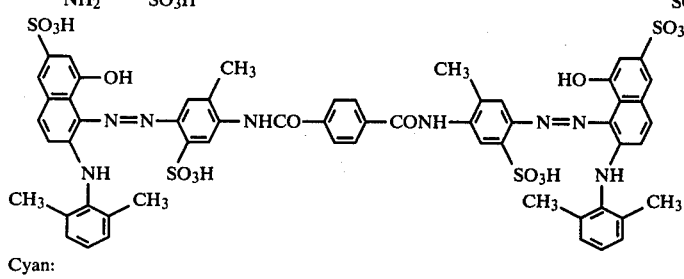
(119)

Cyan:

-continued

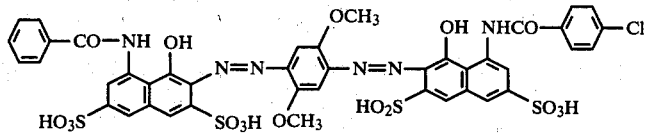 (120)

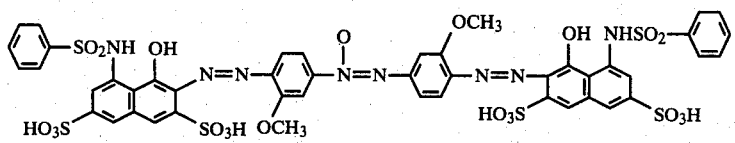 (121)

Coatings, which correspond to the above data, on opaque triacetate film are exposed behind a step wedge and then processed at 24° C., as follows:

| | |
|---|---|
| Developing bath | 6 minutes |
| Washing | 4 minutes |
| Dye bleach bath | 7 minutes |
| Washing | 2 minutes |
| Silver bleach bath | 2 minutes |
| Washing | 2 minutes |
| Fixing bath | 8 minutes |
| Washing | 6 minutes |
| Drying | |

A conventional black-and-white developer is used in the developing bath and baths of customary composition are also used as the silver bleach bath and the fixing bath. The dye bleach bath contains the following components: 28 ml of concentrated sulphuric acid, 1 ml of thioglycerol, 9 g of sodium iodide and 1 mmol of the dye bleach catalyst of the formula (111), per liter of solution.

As a result of processing, a sharp yellow or magenta or cyan step wedge is obtained, depending on the dyestuff. Similar results are also obtained with other catalysts of Tables I to III.

EXAMPLE 2

Single layer coatings according to Example 1 are exposed behind a step wedge and then processed at 24° C., as follows:

| | |
|---|---|
| Developing bath | 6 minutes |
| Washing | 4 minutes |
| Bleach bath | 6 minutes |
| Washing | 2 minutes |
| Fixing bath | 8 minutes |
| Washing | 6 minutes |
| Drying | |

A conventional black-and-white developer is used as the developing bath and a conventional fixing bath is used as the fixing bath. The bleach bath contains the following components: 28 ml of concentrated sulphuric acid, 1 ml of thioglycerol, 9 g of sodium iodide, 10 mmols of m-nitrobenzenesulphonic acid and 5 mmols of the catalyst of the formula (108), per liter of solution.

As a result of processing, a sharp yellow or magenta or cyan step wedge is obtained, depending on the dyestuff. Analogous results are also obtained with other combinations of the catalysts from Tables I to III and the oxidising agents of the formula (18).

EXAMPLE 3

A photographic material with three colour layers for the silver dye bleach process is prepared on a cellulose acetate carrier; it contains, in the lowest, red-sensitive layer, the cyan image dyestuff of the formula

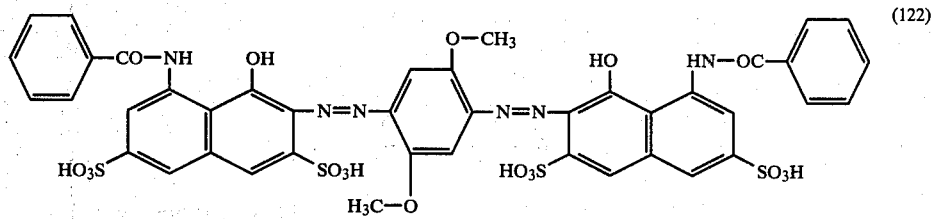 (122)

in the green-sensitive layer above the preceding layer, the magenta image dyestuff of the formula (118) and in the uppermost, blue-sensitive layer, the yellow image dyestuff of the formula (117).

The image dyestuffs are incorporated into the emulsions so as to give a reflection density of D=2.0. The colour layers, containing a total of 0.8 g of Ag/m², are separated by gelatine layers and the total thickness is 15μ.

This material is exposed through a step wedge and then processed as follows:

| | | |
|---|---|---|
| 1. Silver developing bath | | |
| Sodium polyphosphate | 2 | g/l |
| Anhydrous sodium sulphite | 50 | g/l |
| Hydroquinone | 6 | g/l |
| Sodium metaborate | 15 | g/l |
| Borax | 15 | g/l |
| 1-Phenyl-3-pyrazolidinone | 0.25 | g/l |
| Potassium bromide | 1 | g/l |
| Benztriazole | 0.1 | g/l |
| 2. Bleach bath | | |
| 96% strength sulphuric acid | 28 | ml/l |
| Thioglycerol | 1 | ml/l |
| Sodium iodide | 9 | g |
| 2-Amino-4-methyl-5-nitrobenzene-sulphonic acid (ammonium salt) | 5 | g/l |
| Catalyst: compound of the formula (105) | 1.1 | g/l |
| 3. Fixing bath | | |
| 60% strength ammonium thiosulphate | 315 | ml/l |
| 60% strength ammonium bisulphite | 46 | ml/l |
| 25% strength ammonia | 20 | ml/l |

-continued (aqueous solutions each).
4. Washing

After drying, a clear neutral grey image of the subject used is obtained, the exposed regions having been bleached to pure white. Similar results are obtained when other combinations of the catalysts from Tables I to III and the oxidising agent of the formula (18) are employed in corresponding amounts.

EXAMPLE 4

A photographic material for the silver dye bleach process is prepared on a pigmented cellulose acetate carrier using the cyan image dyestuff of the formula (122), the magenta image dyestuff of the formula (118) and the yellow image dyestuff of the formula (117).

The material is made up of double layers, as follows (compare German Offenlegungsschrift No. 2,036,918).

| |
|---|
| blue-sensitive, colourless |
| blue-sensitive, yellow dyestuff (117) |
| yellow filter |
| green-sensitive, colourless |
| green-sensitive, magenta dyestuff (118) |
| intermediate layer (gelatine) |
| red-sensitive, cyan dyestuff (122) |
| red-sensitive, colourless |
| carrier, opaque |

The image dyestuffs are incorporated into the coatings so as to give a reflection density of D=2.0. The total silver content of the three-colour material is 2.0 g of Ag/m² and the total thickness of the photographic layers is 22μ.

In an enlarger, an image of a coloured transparency is projected onto the material. Processing is then carried out in accordance with the following instructions (bath temperature 24° C.):

| 1. Silver developing bath: 2 minutes | | |
|---|---|---|
| Composition | | |
| Sodium polyphosphate | 1 | g/l |
| anhydrous sodium sulphite | 40 | g/l |
| Hydroquinone | 10 | g/l |
| Sodium metaborate | 20 | g/l |
| Sodium hydroxide | 3 | g/l |
| 1-Phenyl-3-pyrazolidinone | 1 | g/l |
| Potassium bromide | 1.5 | g/l |
| Benztriazole | 0.2 | g/l |
| 2. Bleach bath: 4 minutes | | |
| Composition | | |
| Sulphamic acid | 100 | g/l |
| Ascorbic acid | 2 | g/l |
| Ammonium iodide | 7 | g/l |
| Sodium salt of m-nitrobenzene sulphonic acid | 10 | g/l |
| Catalyst: | | |
| Compound of the formula (112) | 3 | g/l |
| 3. Fixing bath: 4 minutes | | |
| Composition | | |
| Ammonium thiosulphate | 220 | g |
| Sodium metabisulphite | 10 | g |
| Sodium sulphite | 40 | g |
| 4. Washing: 6 minutes | | |
| Total processing time | 16 minutes | |

After drying, a print of the colour transparency is obtained which is true in colour and tonality.

Similar results can be achieved when a bleach bath is used which, for example, is prepared from two liquid concentrates according to the following instructions:

| Composition of 1 l of the solution used: | |
|---|---|
| Water | 800 ml |
| Part A | 100 ml |
| Part B | 100 ml |
| Composition part A: | |
| 96% strength sulphuric acid | 20 ml |
| The sodium salt of m-nitrobenzene-sulphonic acid | |
| Water to make up to | 100 ml |
| Part B: | |
| Ethylene glycol monoethyl ether | 65 ml |
| Compound of the formula (112) | 3 g |
| Ascorbic acid | 3 g |
| Potassium iodide | 6 g |
| Water to make up to | 100 ml |

Other catalysts given in Tables I to III can also be employed as catalysts, in place of the compound of the formula (112) with an equally good result.

EXAMPLE 5

A photographic material containing the dyestuffs according to Example 4 is used.

The image dyestuffs are incorporated into the emulsions so as to give a reflection density of D=2.0. The colour layers, containing a total of 0.8 g of Ag/m², are separated by gelatine layers and the total thickness of the 8 layers is 15μ.

This material is exposed in a reproduction camera and then processed in a so-called roll processor. This apparatus consists of 4 tanks, each of 2 liters capacity. The speed of the drive system is so adjusted that the immersion time per tank is 60 seconds. The exposed material passes through the 4 tanks containing the following process solutions and the temperature of the baths is 35° C.:

| 1st Tank - silver developing bath | | |
|---|---|---|
| Composition | | |
| Sodium polyphosphate | 1 | g/l |
| Anhydrous sodium sulphite | 40 | g/l |
| Hydroquinone | 10 | g/l |
| Sodium metaborate | 20 | g/l |
| Sodium hydroxide | 3 | g/l |
| 1-Phenyl-3-pyrazolidinone | 1 | g/l |
| Potassium bromide | 1.5 | g/l |
| Benztriazole | 0.2 | g/l |
| Compound of the formula (103) | 0.4 | g/l |
| 2nd Tank - bleach bath | | |
| Composition | | |
| 96% strength sulphuric acid | 20 | ml/l |
| 4-Mercaptobutyric acid | 1 | ml/l |
| Potassium iodide | 10 | g |
| Sodium salt of m-nitrobenzene-sulphonic acid | 7 | g |
| Compound of the formula (103) | | |
| 3rd Tank - fixing bath | | |
| Composition | | |
| Ammonium thiosulphate | 220 | g |
| Sodium metabisulphite | 10 | g |
| Sodium sulphite | 40 | g |
| 4th Tank - washing bath | | |
| Total processing time (including transport time from tank to tank and with equal dwell time of about 1 minute in the individual tnaks). | 5 minutes | |

After drying, reproductions of the recorded subjects are obtained which are true to nature in colour and tonality. With one filling of the tank it is possible to develop 40 to 60 images 18 cm×24 cm in size in the course of 14 days; the quality of the images is virtually unchanged.

The other compounds given in Tables I to III can also be employed, in place of the compound of the formula (103) with an equally good result.

We claim:

1. A quinoxaline, which corresponds to the formula

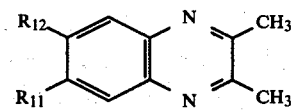

in which $R_{11}$ is methyl or ethyl and $R_{12}$ is —OH, —OCH$_3$, —NHCOCH$_3$ or —NHSO$_2$CH$_3$.

2. A quinoxaline according to claim 1, which corresponds to the formula

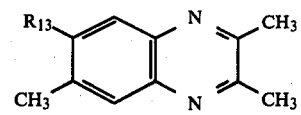

in which $R_{13}$ is —OH, —OCH$_3$, or —NHCOCH$_3$.

3. A quinoxaline according to claim 1, which corresponds to the formula

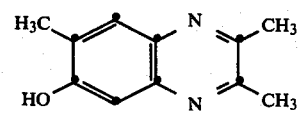

* * * * *